United States Patent [19]

Völkl et al.

[11] Patent Number: 4,581,920
[45] Date of Patent: Apr. 15, 1986

[54] ARRANGEMENT FOR MEASURING EX-VIVO BLEEDING TIME

[75] Inventors: Klaus-Peter Völkl, Robert-Koch-Str. 28, D-4400 Münster; Heinz Schröer, Münster, both of Fed. Rep. of Germany

[73] Assignee: Klaus-Peter Völkl, Münster, Fed. Rep. of Germany

[21] Appl. No.: 660,415

[22] Filed: Oct. 12, 1984

[30] Foreign Application Priority Data

Oct. 15, 1983 [DE] Fed. Rep. of Germany ....... 3337618

[51] Int. Cl.⁴ .......................................... G01N 33/48
[52] U.S. Cl. ...................................... 73/64.1; 73/53
[58] Field of Search ................... 73/64.1, 53; 356/39; 128/632, 637

[56] References Cited

U.S. PATENT DOCUMENTS

| | | | |
|---|---|---|---|
| 3,467,862 | 9/1969 | Vatmakher et al. | 73/64.1 |
| 3,486,859 | 12/1969 | Greiner et al. | 73/64.1 |
| 3,699,437 | 10/1972 | Ur | 324/65 P |
| 3,911,728 | 10/1975 | Fixot | 73/64.1 |
| 4,187,462 | 2/1980 | Haker et al. | 324/61 P |
| 4,484,135 | 11/1984 | Ishihara et al. | 128/632 |
| 4,492,462 | 1/1985 | Pross et al. | 73/64.1 |

*Primary Examiner*—Stewart J. Levy
*Assistant Examiner*—Hezron E. Williams
*Attorney, Agent, or Firm*—Michael J. Striker

[57] ABSTRACT

In order to measure an ex-vivo bleeding time, a blood sample is applied on a measuring opening in a support. A pressure difference is created across the measuring opening and then time is measured during which a definite reduction of size of the measuring opening occurs due to aggregation of blood platelets.

9 Claims, 5 Drawing Figures

FIG. 1
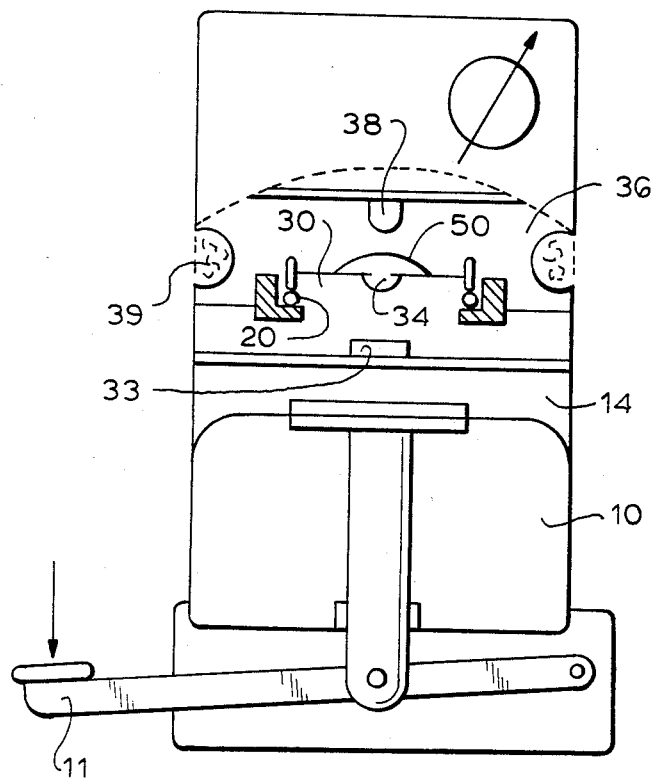
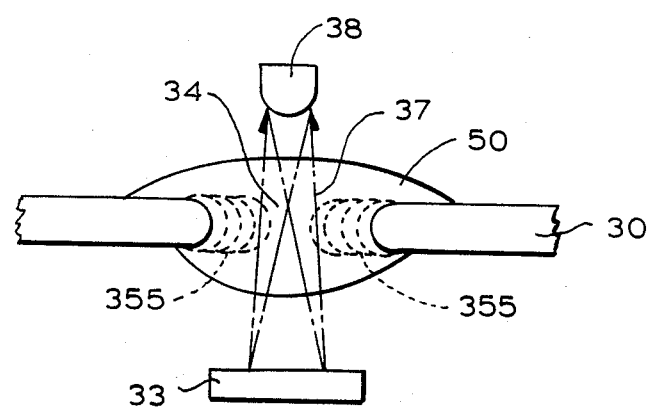
FIG. 3

_ARRANGEMENT FOR MEASURING EX-VIVO BLEEDING TIME_

BACKGROUND OF THE INVENTION

The present invention relates in general to an arrangement for measuring bleeding time out of living organisms.

The closure of wounds in the vessel system of organisms having blood circulation is in general autonomous. In the process, thrombocytes or blood platelets present in the blood liquid aggregate and form together with fibrin a scab which closes the opening and forms a supporting structure for the binding tissue growing thereafter and forming the final closure.

Hitherto it has been assumed that the aggregation of blood platelets results exclusively from freeing of intermediate substances primarily of mediators and enzymes whose formation or actuation is provoked by the wound cells or by changes in hemodynamik.

However, recently it has been found that shearing forces resulting in streaming fluids in the proximity of walls cause at a sufficiently high rate by themselves an aggregation of blood platelets.

SUMMARY OF THE INVENTION

This knowledge permits the measurement of aggregation capability of blood platelets of an individual organism when according to this invention a sample of blood is applied under pressure over a measuring opening and then time is measured during which a definite clearance reduction of the opening occurs.

The arrangement of this invention has the advantage that the aggregation of blood platelets proceeds in the absence of external, physiologically or pharmacologically effective substances. As a consequence, comparative values for different individuals or different conditions of the same individual can be obtained. In the arrangement of this invention, hematocrit and viscosity take effect during the measurement so that these parameters which substantially determine the micro-circulation, can be evaluated individually. On the other hand, the result of measurement is substantially determined by the function of thrombocytes and accordingly the invention presents a test of thrombosis which permits a simple quantification.

Reproduceable results can be reached especially in the case when the test chamber at both sides of the measuring opening is kept moist so that artifacts due to drying process cannot occur.

The bleeding time can be changed by certain diseases, for example by diabetes, or by therapeutically depleted coagulation or anti-coagulation means. By means of the arrangement of this invention it is now possible to measure by a simple test such momentary conditions.

The novel features which are considered as characteristic for the invention are set forth in particular in the appended claims. The invention, however, both as to its construction and its method of operation, together with additional objects and advantages thereof, will be understood from the following description of specific embodiments when read in connection with the accompanying drawing.

BRIEF DESCRIPTION OF THE DRAWING

FIG. 1 is an overall arrangement of this invention using optical means for determining a standard point;

FIG. 3 illustrates a measuring opening of FIG. 1, shown on an enlarged scale;

DESCRIPTION OF THE PREFERRED EMBODIMENTS

Figure 2:
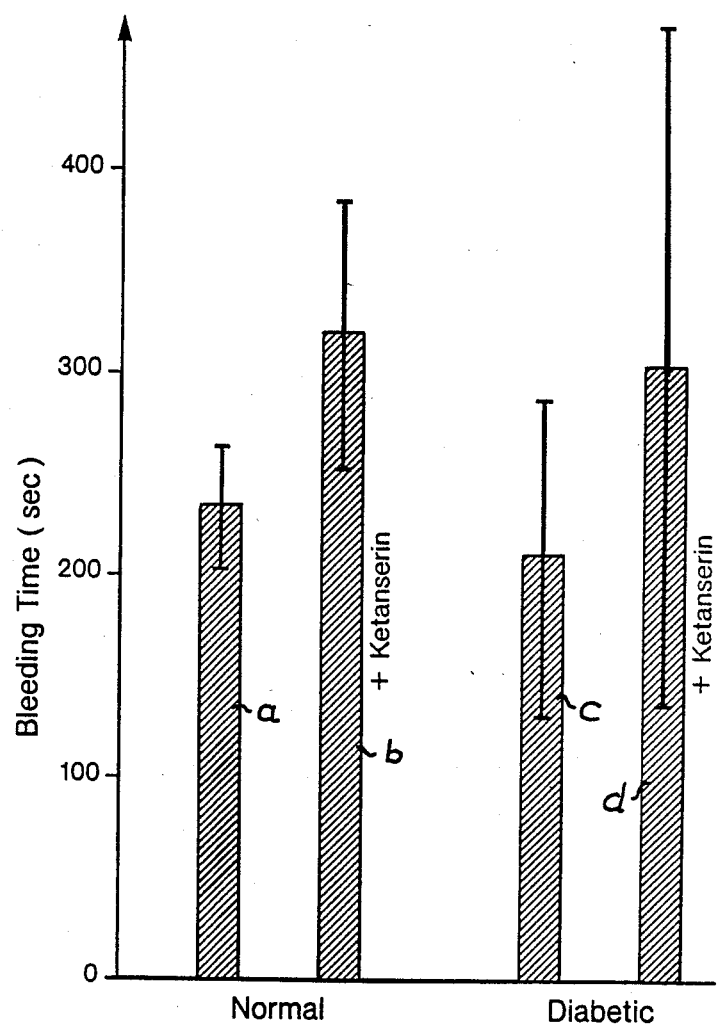
FIG. 2 shows a diagram of test results.

The arrangement for measuring bleeding time ex-vivo or out of living organisms includes a manually operable diaphragm pump 10 formed at its top with an inlet provided on its rim with annular sealing means 20 into which a ring 31 provided with a diaphragm 30 is insertable. The diaphragm 30 has a thickness for example of about 200 micrometers and is provided at its center with a measuring opening 34 having about 0.05 millimeters in diameter. A drop of a blood sample 50 is applied on the diaphragm 30 over the measuring opening 34, the ring 31 is laid upon the sealing ring 20 and the pump 10 is operated by depressing the lever 11 in the direction of arrow and subsequently arrested in a depressed position whereby an underpressure is formed in space 14 below the measuring opening 34. The pressure difference across the measuring opening amounts in this example to about 100 millimeters Hg.

The blood drop 50 is placed in a measuring chamber 36 enclosing also a moist cotton 39 so as to create within the chamber 36 an atmosphere saturated with water vapors. Due to the pressure difference, the blood drop 50 starts to flow into the pressure space 14 of the pump 10. Tangential stress or shearing force acting on the blood flow cause an aggregation of blood platelets in the measuring opening 34 whereby the diameter of the measuring opening is reduced and this reduction is measured.

If pressure air installation or air bottles are available then the diaphragm pump can be dispensed with.

It is also of advantage when the measuring chamber 36 is provided with thermostats to keep a temperature of about 310° K.

The ratio between the diameter of the measuring opening and the thickness of the diaphragm 30 is preferrably about 0.01 to 10. In a variation it is also advantageous to adjust this ratio to the least amount of flow passing through the measuring opening. For instance, if the measuring opening is about 25 micrometers in diameter and the diaphragm thickness is about 100 micrometers, the result of measurement is indicated in the diaphram of FIG. 2. In this test a bleeding time of a normal person is shown (diagram a), of a normal person after depletion of 6.25 micrograms ketanserin per milliliter of blood (diagram b), of a diabetic (diagram c), and of a diabetic after depletion of 6.25 micrograms ketanserin (diagram d).

In FIG. 3, the supporting diaphragm or membrane 30 with a measuring opening 34 is illustrated on an enlarged scale.

An electroptic device is used for measuring a reference clearance of the measuring opening 34. The electroptic device includes a light emitting diode 33 arranged in the under pressure space 14 of the pump for emitting light beam 37 through the measuring opening 34 in the membrane 30 and through the blood sample 50 covering the measuring opening. The light beam is then measured by the photoreceiver 38 and indicated by an indicator 361.

The pressure difference across the length of the bore representing the measuring opening causes the desired shearing force in the blood flow which can be computed as follows:

With
r = Radius of measuring opening
i = Blood flow rate
L = Length of measuring opening
dp = Pressure difference
Q = Cross section of the measuring opening
v = Average velocity of flow
M = Viscosity
$\gamma$ = Shear rate
$\tau$ = Shearing force
V = Volume $$\tau = M \cdot \gamma \quad (1)$$

With $$M = \frac{\pi \cdot dp \cdot r^4}{8 l} \cdot \frac{t}{V} \quad (2)$$

With the shear rate $$\gamma = \frac{4\bar{v}}{r} \quad (3)$$

The results $$\tau = \frac{\pi \cdot dp \cdot r^3}{2 l} \cdot \frac{t}{V} \bar{v} \quad (4)$$

With respect $$\frac{V}{t} = \bar{v} \cdot Q \quad (5)$$

The resulting shearing force is $$\tau = \frac{dp \cdot r}{2 \cdot L} \quad (6)$$

With the following selected magnitudes
r (m) = 25
dp (N/m$^2$) = 9600
L (cm) = 0.02
Q (cm$^2$) = 1.96*10exp−5
V (cm/s) = 7.4−4.9*10exp−3
there results a shearing force of about 600 N/m$^2$.

The light throughput through the measuring opening 34 as described before, is reduced proportionally to the aggregated blood platelets in the measuring opening.

The final result of measurement is obtained when no blood passes through the measuring opening 34. The time period necessary for reaching this condition is of a wanted unknown value.

Alternatively, it is also possible to preset a certain time period and the measured lumen variation or the change in size of the diameter of the measuring opening is determined.

The latter method has the advantage that the determination of the wanted value is more accurate inasmuch as the measuring process need not be continued until a complete stand still of the blood flow is reached.

Figure 4:
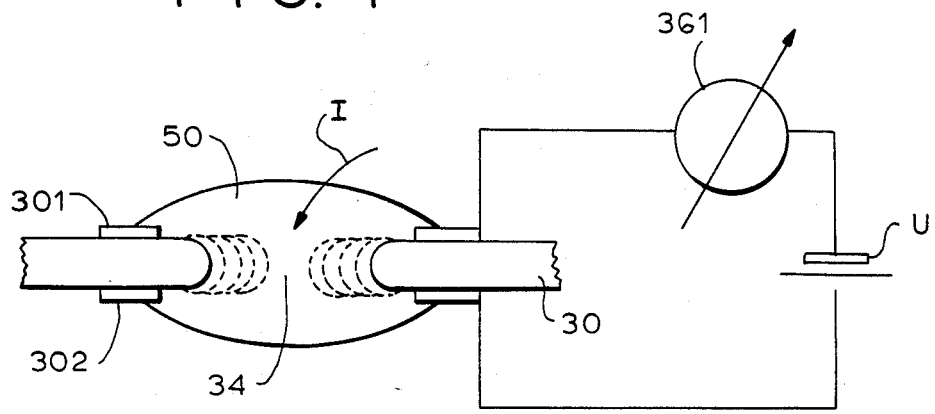
FIG. 4 is a modification of FIG. 3 wherein the standard point is determined by electrical means.

In FIG. 4, the lumen change of the measuring opening is determined by measuring conductivity of the blood flow. For this purpose, the membrane 30 which is made of an insulating material is provided on both sides with metalized layers 301, 302 and a direct current voltage U is applied to the metalized electrodes. Electric current I then flows exclusively through the measuring opening 34. The reduction of the diameter of the measuring opening caused by the aggregation 355 of blood platelets is determined by the corresponding change of resistance indicated by a measuring instrument 361.

Figure 5:
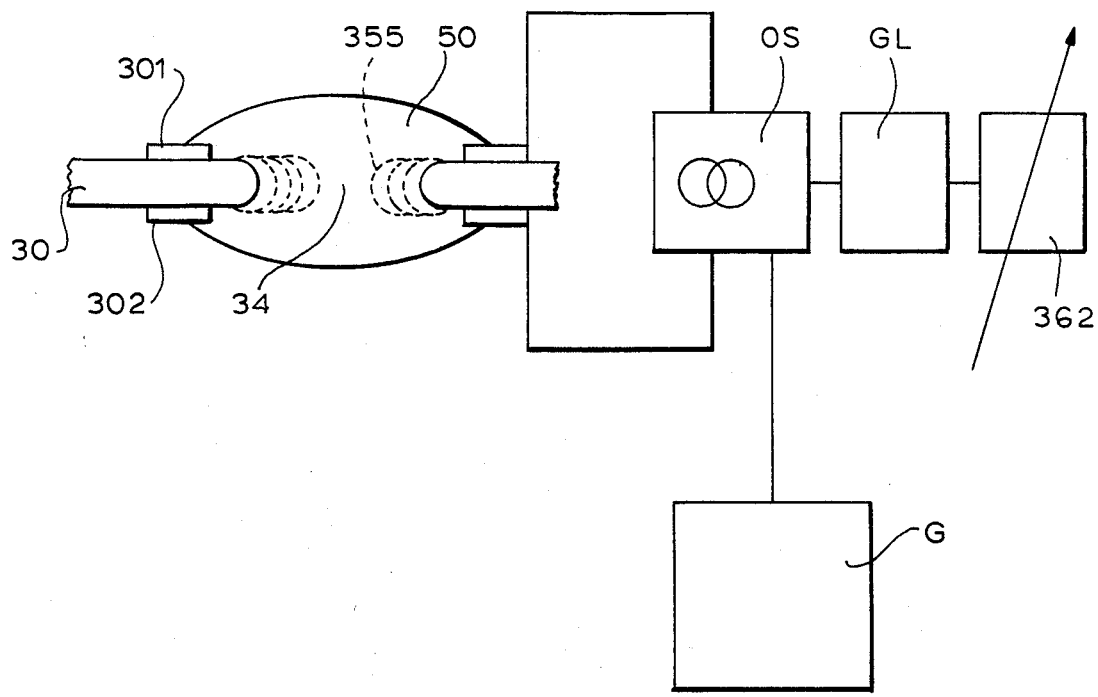
FIG. 5 is a another modification of FIG. 3 wherein the standard point is determined by an oscillatory circuit.

According to FIG. 5, the change in the lumen of the measuring opening can be also determined from the change of the resonance curve of an oscillator OS. For this purpose, the electrodes 301, 302 on the membrane 30 are utilized as a capacitor in an oscillating circuit. Due to the aggregation 355 of blood platelets the frequency of the tank circuit 301, 302 and 50 is changed and upon mixing of the signal with the signal of a local oscillator G, the resulting oscillations are rectified by a rectifier GL and measured by a measuring instrument 362.

It will be understood that each of these elements described above, or two or more together, may also find a useful application in other types of constructions differing from the types described above.

While the invention has been illustrated and described as embodied in specification examples of the measuring arrangement, it is not intended to be limited to the details shown since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An arrangement for measuring bleeding time out of a living organism, comprising a support including a membrane of a thickness of about 200 micrometers, the membrane being provided with a measuring opening for receiving a sample of blood applied thereover; means for applying pressure on the blood sample to cause a flow of blood through the measuring opening; the size of the measuring opening being sufficiently small to develop a shearing force acting on individual blood platelets in the blood flow; and means for measuring time of a size reduction of the measuring opening caused by aggregation of blood platelets due to the shearing force.

2. An arrangement as defined in claim 1 wherein the support is enclosed in a measuring chamber including moistening means for saturating the atmosphere within the champer up to 100% with water vapors.

3. An arrangement as defined in claim 1 wherein the membrane is of an insulating material formed with the measuring opening, and said time measuring means including metallic electrodes on opposite sides of the membrane and means for measuring conductivity of the blood through the measuring opening.

4. An arrangement as defined in claim 1 wherein the membrane is of a nonconductive material formed with the measuring opening and provided at opposite sides thereof with metallic electrodes, and the time measuring means comprising a tank circuit including the electrodes of the membrane and means for measuring changes of the resonance curve of the tank circuit caused by the changes of capacity due to the changes in the measuring opening.

5. An arrangement as defined in claim 1 wherein the time measuring means includes a light source arranged at one side of the measuring opening, a light receiver arranged opposite the other side of the measuring opening and means for indicating the amount of light detected by the light receiver.

6. An arrangement as defined in claim 1 wherein said means for applying pressure includes a hand operated pump connected to one side of the support.

7. An arrangement as defined in claim 1 wherein the ratio of the diameter of the measuring opening to the thickness of the membrane is between 0.01 and 10.

8. An arrangement as defined in claim 2 wherein the measuring chamber is provided with a thermostat.

9. An arrangement as defined in claim 8 wherein the thermostat keeps the temperature within the measuring chamber to about 310° K.

* * * * *